(12) United States Patent
Imran (10) Patent No.: US 8,744,569 B2
(45) Date of Patent: *Jun. 3, 2014

(54) IONTOPHORETIC SYSTEM FOR TRANSDERMAL DELIVERY OF ACTIVE AGENTS FOR THERAPEUTIC AND MEDICINAL PURPOSES

(75) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/481,466

(22) Filed: May 25, 2012

(65) Prior Publication Data

US 2012/0232464 A1   Sep. 13, 2012

Related U.S. Application Data

(63) Continuation of application No. 12/537,243, filed on Aug. 6, 2009, now Pat. No. 8,190,252.

(60) Provisional application No. 61/152,251, filed on Feb. 12, 2009.

(51) Int. Cl.
*A61N 1/30* (2006.01)

(52) U.S. Cl.
USPC .............................. 604/20; 604/501

(58) Field of Classification Search
USPC .................................. 604/501, 20
See application file for complete search history.

(56) References Cited

U.S. PATENT DOCUMENTS

| | | | |
|---|---|---|---|
| 3,491,187 A | 1/1970 | Ely | |
| 4,325,367 A | 4/1982 | Tapper | |
| 4,731,049 A | 3/1988 | Parsi | |
| 4,734,090 A | 3/1988 | Sibalis | |
| 4,886,489 A | 12/1989 | Jacobsen et al. | |
| 5,207,752 A | 5/1993 | Sorenson et al. | |
| 5,310,404 A | 5/1994 | Gyory et al. | |
| 5,322,502 A | 6/1994 | Theeuwes et al. | |

(Continued)

FOREIGN PATENT DOCUMENTS

| | | |
|---|---|---|
| CN | 1606461 A | 4/2005 |
| CN | 101036825 A | 9/2007 |
| EP | 0090425 A1 | 10/1983 |

OTHER PUBLICATIONS

U.S. Appl. No. 12/898,671, filed Oct. 5, 2010, Imran.

(Continued)

*Primary Examiner* — Kevin C Sirmons
*Assistant Examiner* — Deanna K Hall
(74) *Attorney, Agent, or Firm* — Mahamedi Paradice Kreisman LLP (57) ABSTRACT

An embodiment of a system includes a power source and at least two electrode assemblies. The power source that an output current that alternates between a maximum current value and a minimum current value; a pair of electrode assemblies. Each electrode assembly is configured to be held in contact with a skin layer of a user. Additionally, each electrode assembly includes an electrode that is coupled to the power source to receive the output current from the power source. At least one of the electrode assemblies in the pair includes a medium that carries an active agent having a charge, the medium being provided on the at least one electrode assembly to enable the output current to repel the active agent into the skin layer for a duration in which the output current has a polarity that is the same as a polarity of the active agent.

17 Claims, 5 Drawing Sheets

(56) References Cited

U.S. PATENT DOCUMENTS

| | | | |
|---|---|---|---|
| 5,328,453 A | 7/1994 | Sibalis | |
| 5,385,543 A | 1/1995 | Haak et al. | |
| 5,503,632 A | 4/1996 | Haak | |
| 5,605,536 A | 2/1997 | Sibalis | |
| 5,693,024 A | 12/1997 | Flower | |
| 5,797,867 A | 8/1998 | Guerrera et al. | |
| 5,830,175 A | 11/1998 | Flower | |
| 5,928,185 A | 7/1999 | Muller et al. | |
| 5,983,130 A | 11/1999 | Phipps et al. | |
| 6,018,679 A | 1/2000 | Dinh et al. | |
| 6,018,680 A | 1/2000 | Flower | |
| 6,019,877 A | 2/2000 | Dupelle et al. | |
| 6,064,908 A | 5/2000 | Muller et al. | |
| 6,330,471 B1 | 12/2001 | Higo et al. | |
| 6,512,950 B2 * | 1/2003 | Li et al. | 604/20 |
| 6,553,255 B1 | 4/2003 | Miller et al. | |
| 6,689,275 B1 | 2/2004 | Gupta | |
| 6,726,920 B1 * | 4/2004 | Theeuwes et al. | 424/423 |
| 6,731,965 B2 | 5/2004 | Menon et al. | |
| 6,779,468 B1 | 8/2004 | Gupta | |
| 7,137,975 B2 | 11/2006 | Miller et al. | |
| 7,340,297 B2 | 3/2008 | Tamarkin et al. | |
| 7,375,139 B2 | 5/2008 | Aldred | |
| 7,437,189 B2 | 10/2008 | Matsumura et al. | |
| 7,496,401 B2 | 2/2009 | Bernabei | |
| 7,522,954 B2 | 4/2009 | Tedoldi | |
| 7,548,778 B2 | 6/2009 | Roy | |
| 7,558,625 B2 | 7/2009 | Levin et al. | |
| 7,590,444 B2 | 9/2009 | Tanioka et al. | |
| 7,593,770 B2 | 9/2009 | Lerner | |
| 7,611,481 B2 | 11/2009 | Cleary et al. | |
| 7,816,404 B2 | 10/2010 | McCall, Jr. | |
| 8,190,252 B2 * | 5/2012 | Imran | 604/20 |
| 8,348,922 B2 | 1/2013 | Imran | |
| 8,417,330 B2 | 4/2013 | Imran | |
| 8,423,131 B2 | 4/2013 | Imran | |
| 2003/0060798 A1 | 3/2003 | Fischer et al. | |
| 2003/0199808 A1 | 10/2003 | Henley et al. | |
| 2004/0138646 A1 | 7/2004 | Walla | |
| 2005/0020487 A1 | 1/2005 | Klaus et al. | |
| 2005/0085751 A1 | 4/2005 | Daskal et al. | |
| 2005/0165393 A1 | 7/2005 | Eppstein | |
| 2005/0209565 A1 | 9/2005 | Yuzhakov | |
| 2005/0213286 A1 | 9/2005 | Michel et al. | |
| 2005/0238704 A1 | 10/2005 | Zumbrunn et al. | |
| 2005/0273046 A1 | 12/2005 | Kwiatkowski et al. | |
| 2006/0025715 A1 | 2/2006 | Henley et al. | |
| 2006/0216339 A1 | 9/2006 | Ambron et al. | |
| 2006/0229549 A1 | 10/2006 | Hause et al. | |
| 2006/0258973 A1 | 11/2006 | Volt | |
| 2007/0065521 A1 | 3/2007 | Venkataraman et al. | |
| 2007/0066934 A1 | 3/2007 | Etheredge et al. | |
| 2007/0083185 A1 | 4/2007 | Carter | |
| 2007/0083186 A1 | 4/2007 | Carter et al. | |
| 2007/0224253 A1 | 9/2007 | Franklin | |
| 2008/0027369 A1 | 1/2008 | Carter et al. | |
| 2008/0058699 A1 | 3/2008 | Hause et al. | |
| 2008/0058700 A1 | 3/2008 | Hause et al. | |
| 2008/0081051 A1 | 4/2008 | Sabin et al. | |
| 2008/0114282 A1 | 5/2008 | Carter | |
| 2008/0154178 A1 | 6/2008 | Carter et al. | |
| 2008/0287497 A1 | 11/2008 | Anderson et al. | |
| 2009/0036821 A1 | 2/2009 | Lai | |
| 2009/0062720 A1 | 3/2009 | Anderson et al. | |
| 2009/0124572 A1 | 5/2009 | Nelson | |
| 2009/0163597 A1 | 6/2009 | Goto et al. | |
| 2009/0171313 A1 | 7/2009 | Yamamoto et al. | |
| 2009/0221985 A1 | 9/2009 | Bukshpan et al. | |
| 2009/0254018 A1 | 10/2009 | Nakayama | |
| 2009/0259176 A1 | 10/2009 | Yairi | |
| 2009/0281475 A1 | 11/2009 | Nisato et al. | |
| 2009/0299264 A1 | 12/2009 | Matsumura et al. | |
| 2009/0299267 A1 | 12/2009 | Durand | |
| 2010/0204637 A1 | 8/2010 | Imran | |
| 2010/0331759 A1 | 12/2010 | Imran | |
| 2010/0331811 A1 | 12/2010 | Imran | |
| 2011/0082411 A1 | 4/2011 | Imran | |
| 2012/0232464 A1 | 9/2012 | Imran | |
| 2013/0023815 A1 | 1/2013 | Imran | |
| 2013/0023850 A1 | 1/2013 | Imran | |

OTHER PUBLICATIONS

Murhty et al., "Irontophoresis™: Transdermal Delivery of Iron by Iontophoresis," J. Pharm. Sci., 98(8): 2670-2676 (Aug. 2009).
International Search Report, Written Opinion and Notice of Transmittal of Same mailed Sep. 27, 2010 in PCT/US2010/023112.
International Search Report, Written Opinion and Notice of Transmittal of Same mailed Sep. 27, 2010 in PCT/US2010/023744.
Non-Final Office Action mailed Apr. 8, 2011 in U.S. Appl. No. 12/537,243.
International Search Report, Written Opinion and Notice of Transmittal of Same mailed Jun. 24, 2011 in PCT/US2010/051541.
International Preliminary Report on Patentability mailed Aug. 25, 2011 in PCT/US2010/023744.
International Preliminary Report on Patentability mailed Aug. 25, 2011 in PCT/US2010/023112.
International Search Report, Written Opinion and Notice of Transmittal of Same mailed Feb. 25, 2011 in PCT/US2010/040109.
Final Office Action mailed Oct. 28, 2011 in U.S. Appl. No. 12/537,243.
Notice of Allowance mailed Jan. 19, 2012 in U.S. Appl. No. 12/537,243.
International Preliminary Report on Patentability mailed Jan. 12, 2012 in PCT/US2010/040109.
Non-Final Office Action mailed Mar. 23, 2012 in U.S. Appl. No. 12/658,637.
International Preliminary Report on Patentability as issued in related International application PCT/US2010/051541, dated Apr. 19, 2012.
Non-final Office Action mailed in U.S. Appl. No. 12/824,147, dated Jun. 1, 2012.
Non-final Office Action mailed in U.S. Appl. No. 12/824,146, dated Jun. 1, 2012.
Notice of Allowance issued in U.S. Appl. No. 12/658,637, dated Jul. 9, 2012.
McLaughlin, G.W., et al., "Biphasic Transdermal Iontophoretic Drug Delivery Platform," Conf. Proc. IEEE Eng. Med. Biol. Soc. Aug. 2011; 2011:1225-8.
International Search Report and Written Opinion as issued in corresponding application PCT/US2012/030633, dated Oct. 31, 2012.
Notice of Allowance issued in U.S. Appl. No. 12/658,637, dated Aug. 31, 2012.
Non-Final Office Action of Dec. 12, 2012 in U.S. Appl. No. 12/898,671.
Notice of Allowance of Nov. 30, 2012 in U.S. Appl. No. 12/824,146.
Notice of Allowance of Nov. 23, 2012 in U.S. Appl. No. 12/824,127.
Examination Report mailed Aug. 13, 2013 in Australian Application No. 2010213975.
Office Action mailed Jul. 19, 2013 in Chinese Application No. 1080013328.7.
Final Office Action mailed Jul. 11, 2013 in U.S. Appl. No. 12/898,671.
U.S. Appl. No. 14/024,539, filed Sep. 11, 2013, Imran et al.

* cited by examiner

IONTOPHORETIC SYSTEM FOR TRANSDERMAL DELIVERY OF ACTIVE AGENTS FOR THERAPEUTIC AND MEDICINAL PURPOSES

RELATED APPLICATIONS

This application is a Continuation of U.S. application Ser. No. 12/537,243, filed Aug. 6, 2009 and Issued as U.S. Pat. No. 8,190,252 on May 29, 2012, entitled "Iontophoretic System for Transdermal Delivery of Active Agents for Therapeutic and Medicinal Purposes", which claims the benefit of priority to Provisional U.S. Patent Application No. 61/152,251, entitled "Kit, System and Method for Transdermal Iontophoretic Delivery of Therapeutic Agents", filed Feb. 12, 2009; all of the aforementioned priority applications being hereby incorporated by reference in their respective entirety for all purposes.

FIELD OF THE INVENTION

Embodiments described herein relate to iontophoretic transdermal delivery of active agents for therapeutic purposes.

BACKGROUND

Iontophoresis is a non-invasive method of propelling high concentrations of a charged substance, known as the active agent, transdermally by repulsive electromotive force using a small electrical charge. This method has been used for the transdermal delivery of various compounds including therapeutic agents. Traditionally, direct current has been used to provide the driving current for iontophoresis. However there are a number of short comings associated with the use of direct current including limitations on the total amount of current that can be delivered over time without causing injury to the skin, as well as the build up of capacitive charge in the skin layer which can oppose the electromotive driving forces thus reducing the rate and total amount of compound delivered over time. Also direct current can cause a local anesthetic effect to the skin resulting in burns and other thermal damage to the skin because the user doesn't feel the injury to the skin occurring at the time. Thus there is need for improved methods for delivering various therapeutic agents using transdermal iontophoresis.

DETAILED DESCRIPTION OF THE INVENTION

Embodiments described herein provide for an iontophoretic system for transdermal delivery of drugs and other therapeutic agents. As used herein, the term transdermal refers to the delivery of a compound, such as a drug or other biological agent, through one or more layers of the skin (e.g., epidermis, dermis, etc). Iontophoresis is a non-invasive method of propelling high concentrations of a charged substance, known as the active agent, transdermally using electrical current applied at the skin layer. The active agent can include a drug or other therapeutic agent or biological compound.

More specifically, embodiments described herein include a system for transdermal delivery of active agents for therapeutic and medicinal purposes. The system includes a power source and at least two electrode assemblies. The power source provides an output current that alternates between a maximum current value and a minimum current value; a pair of electrode assemblies. Each electrode assembly is configured to be held in contact with a skin layer of a user. Additionally, each electrode assembly includes an electrode that is coupled to the power source to receive the output current from the power source. At least one of the electrode assemblies in the pair includes a medium that carries an active agent having a charge, the medium being provided on the at least one electrode assembly to enable the output current to repel the active agent into the skin layer for a duration in which the output current has a polarity that is the same as a polarity of the active agent.

According to one or more embodiments, an output current such as described is a charged balanced alternating current (AC) output. The charged balance AC output means over a given duration, the amount of current delivered at each polarity is substantially equivalent. As used herein substantially equivalent means that two values are within 80% of one another, and more preferably within 90% or 99% over the period of one or more waveforms.

Single Point Disbursement

Figure 1:
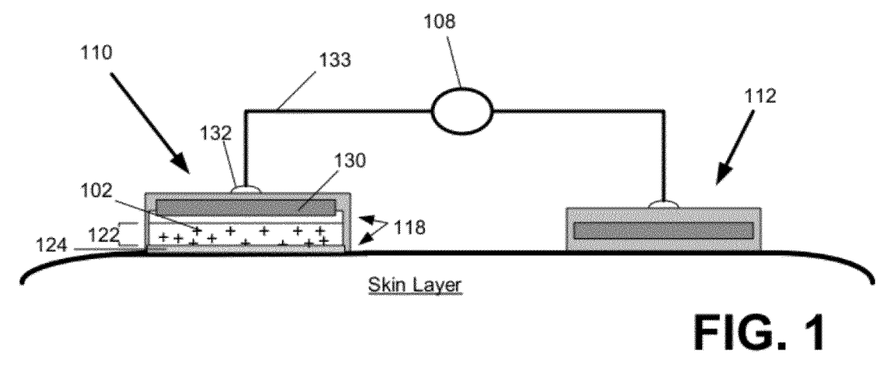
FIG. 1 illustrates an iontophoretic system for transdermal delivery of an active agent, according to one or more embodiments.

FIG. 1 illustrates an iontophoretic system for transdermal delivery of an active agent, according to one or more embodiments. A system 100 is shown in a deployed (i.e. operational) state, and comprises a pair of active electrode assemblies 110, 112 and alternating power source 108 that combine to enable the transdermal delivery of a medicinal or therapeutic ("active") agent 102 into a user's tissue. Therapeutic agent 102 can comprise one or more drugs or other therapeutic agents. In the deployed state, the pair of electrode assemblies 110, 112 are positioned on the exterior skin layer of the user. In one embodiment, the alternating power source 108 forces the agent 102 to be dispensed from one of the electrode assemblies in the pair (shown as electrode assembly 110 in FIG. 1). More specifically, the active agent 102 is selected to have an ionic charge, and the alternating power source 108 is connected to electrode assembly 110 to repel the active agent 102 into the skin layer of the user at instances when the alternating power source has the same polarity as the active agent. As such, the driving mechanism that causes the active agent 102 to dispense into the skin layer is intermittent and alternating (to match the output of the power source 108).

With specific reference to FIG. 1, the power source 108, electrode assemblies 110, 112 and user skin layer or tissue form a circuit to enable delivery of the active agent from at least one of the electrode assemblies. More specifically, FIG. 1 illustrates a single disbursement configuration in which the first electrode assembly 110 contains the active agent, and the second electrode assembly 112 serves as a return without the active agent. In the configuration shown, the second electrode assembly 112 serves as the return for completing the circuit with power source 108 and the first electrode assembly 110. For a duration, the output current is provided a polarity that matches that of the charge of the active agent. The presence of the output current, flowing via the circuit formed by the other electrode assembly and the power source 108, results in the charged active agent being repulsed from the electrode assembly 110 into the skin layer of the user. Thus, in a configuration shown by FIG. 1, the first active electrode assembly 110 is equipped with the active agent 102, and the power source 108 directs the active agent from the first electrode assembly 110 into the skin layer when the polarity of the output current matches that of the charge of the active agent.

As described below, the power source 108 may vary the output of the current output to alternate durations in which the active agent is delivered. In one embodiment, the power source 108 varies the output current between a maximum current value (coinciding with a delivery duration) and a minimum current value (coinciding with non-delivery duration). The minimum current value corresponds to either no current output, or a reverse current output. As described elsewhere, the reverse current output may serve as a retention mechanism that actively precludes the active agent from diffusing into the skin layer (e.g., due to electrostatic attractive forces). Thus, a delivery duration coincides with a duration in which an output current from the power source 108 has polarity to match that of the active agent. A non-delivery duration coincides with either an output current from the power source that is opposite in polarity to that of the active agent, or to a duration that coincides with substantially no current output.

In a system such as described with FIG. 1, some embodiments provide for the delivery/non-delivery durations to be symmetrical or equal. For example, delivery/non-delivery durations may each last x milliseconds, seconds, or minutes, to match, for example, symmetrical waveforms of the output (e.g. sinusoidal, square wave etc.). In other embodiments, the delivery/non-delivery durations are asymmetrical or unequal. For example, the delivery duration may last several minutes, and the non-delivery duration may last only seconds or otherwise be less than the delivery duration. The delivery/non-delivery durations may repeat, or pass through only a single cycle (i.e., one delivery duration and one non-delivery duration).

Each electrode assembly 110, 112 includes an electrode 130 and a contact thickness 118. The contact thickness 118 of each electrode assembly 110, 120 may be in form of a patch fabricated from layers of elastomeric or other flexible polymer material. The contact thickness 118 may include, for example, adhesives for enabling the respective electrode assemblies 110, 112 to be deployed on the skin layer of the user and to remain adhered over an extended period of time during movement of the skin. Likewise, the electrode 130 corresponds to one or more elements or layers that extend the conductive path from the alternating power source to the contact thickness and/or skin layer. In one embodiment, a connector 132 connects the electrode 130 to leads 133 of powers source 108. The electrode 130 corresponds to a metal layer or element(s) (e.g. wiring, contact elements etc.) that extends or connects to the connector 132. The electrode 130 may comprise a separate layer from the contact thickness 118, which includes a medium 122 for carrying the active agent 102. However, in some variations, the electrode 130 includes elements, such as particles or contact elements, that are integrated or provided with the contact thickness 118. In one implementation, the electrode 130 is comprised of conductive material, such as metal (e.g. silver) or conductive carbon material (graphite sheets). In an embodiment depicted by FIG. 1, electrode 130 is a conductive layer that overlay the contact thickness 118. As described below, the contact thickness 118 includes thicknesses for dispersing the active agent 102, as well as material to enable the electrode assembly to be adhered to skin. In many embodiments, the active agent is dissolved in an aqueous or other carrier solution, for example, isopropyl alcohol, DMSO and like compounds.

As previously mentioned, in an embodiment of FIG. 1, only one of the electrode assemblies in the pair (shown as electrode assembly 110) is used to deliver the active agent 102 into the user's skin. The medium 122 of the first electrode assembly 110 provides a reservoir or retainer that contains the active agent, for example, in embodiments where the active agent is dissolved in a carrier solution. More specifically, the medium 122 of the contact thickness 118 includes a tissue contacting porous layer 124, which can either be separate or part of a reservoir. The porous layer 124 can be configured to absorb the carrier solution from the reservoir and in turn wick the solution into contact with the skin (e.g. by capillary action). The porosity of the porous layer 124 may be selected based on various parameters. For example, the porosity may be selected based on the concentration or transport characteristics of the active agent. More specifically, for example, high porosities can be selected for higher molecular weight therapeutic agents and/or therapeutic agents solutions having greater viscosity. Suitable porous materials for porous layer 124 can comprise compressed cotton or other fibrous meshe such as meshs made from various polymer fibers The electrode assemblies 110, 112 can be constructed as disposable or reusable. If disposable, the electrode assembly 110 (carrying the active agent) is manufactured or retailed to include the active agent in the medium 122. If reusable, an embodiment provides that the electrode assembly 110 includes an intake conduit and optional self-sealing port that enables the active agent 102 to be dispersed in the medium 122 for delivery. In one embodiment, the self-sealing port is formed from silicone or other elastomeric material, so as to enable the electrode assembly 110 to be filled with the active agent.

The alternating power source 108 may correspond to a battery, such as a rechargeable Lithium-Ion battery pack. As an alternative, the alternating power source 108 may, include or provide an interface, to another power source, such as a solar cell. Circuitry (such as described with FIG. 4) may be used to convert the direct-current (DC) power output to an alternating signal of a specified waveform. As mentioned elsewhere, the specified waveform may be short (e.g. milliseconds), long (minutes), symmetrical (delivery/non-delivery are equal), or asymmetrical (delivery/non-delivery are now equal).

The electrode assemblies 110, 112 and the alternating power source 108 may be provided in connection with one or more housing segments. For example, the power source 108, electrode assemblies 110, 112, and wiring or connectors that interconnect the power source and the electrode assemblies may all be contained by a housing, or combination of integrated housing segments. In this way, the system of electrode assemblies 110, 112 may be provided as a product, device or kit that can be assembled and deployed by the user. The kit may further include instructions for use.

When deployed and made operational, the active agent is selected to have an ionic charge that can be sufficiently repulsed by the presence of current having the same polarity. The active agent is distributed in the medium 122 of the electrode assembly 110. The power source 108 is connected and signaled, resulting in a circuit being formed between the alternating power source 108, electrode assembly 110 containing the active agent, and the electrode assembly 112 providing the return electrode. In the durations when the current has the same polarity as the charge of the active agent, the active agent is repulsed from the medium 122 of the electrode assembly 110 into the skin layer of the user. In the durations when the current has the opposite polarity as the charge of the active agent, the active agent is not repulsed. Thus, the active agent is induced to travel into the skin layer in alternating durations to match the alternating power of the alternating power source 108. The frequency of the alternating power source 108 may vary greatly. In particular, the frequency of the alternating power source may be in the range of milliseconds (e.g. 1/60 seconds) or minutes (e.g. ten minutes).

Among other benefits, the diffusion of the active agent into the skin layer can be completely stopped with the switch in the current polarity. Thus, use of the alternating power source 108 enables the active agent to be stopped from entering the skin layer at alternating instances. This enables, for example, better control of the amount of active agent delivered into the skin layer in a given duration.

Double Point Disbursement

Figure 2:
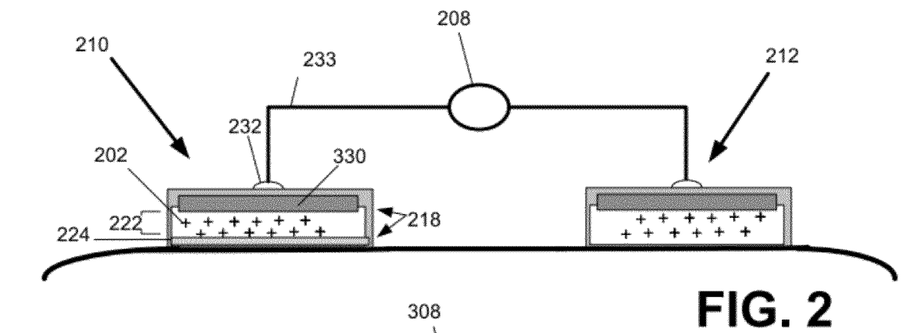
FIG. 2 illustrates an alternative embodiment in which each of a pair of electrode assemblies are equipped to disperse an active agent into the skin layer, under another embodiment.

FIG. 2 illustrates an alternative embodiment in which each of a pair of electrode assemblies are equipped to disperse an active agent into the skin layer, under another embodiment. More specifically, an embodiment of FIG. 2 shows a first and second electrode assembly 210, 212, each of which can include a construction similar to that shown with the first electrode assembly 110 of FIG. 1. Accordingly, the first and second electrode assemblies 210, 212 each include an electrode 230 positioned over or in operative relationship to a contact thickness 218. The contact thickness 218 of each electrode assembly 210, 220 may be in form of a patch fabricated from layers of elastomeric or other flexible polymer material. The contact thickness 218 may include, for example, adhesives for enabling the respective electrode assemblies 210, 212 to be deployed on the skin layer of the user. Likewise, the electrode 230 of each electrode assembly 210, 212 may correspond to one or more metal layer or element(s) (e.g. wiring, contact elements etc.) that extends or connects to a connector 232, which in turn connects that electrode 230 to leads 233 of powers source 208. On each electrode assembly 210, 212, the electrode 230 may comprise a separate layer from the contact thickness 218, which includes a medium 222 for carrying the active agent 202. However, in some variations, the electrode 230 includes elements, such as particles or contact elements, that are integrated or provided with the contact thickness 218. In one implementation, the electrode 230 is comprised of conductive material, such as metal (e.g., silver or siliver-silverchloride) or conductive carbon material (e.g., graphite sheets).

The medium 222 of the electrode assemblies 210, 212 includes a tissue contacting porous layer 224, which can either be separate or part of a reservoir. Similarly, in an implementation in which one or both of the electrode assemblies 210, 212 reusable, a self sealing port (not shown) may be included to enable the active agent to be dispersed in the medium 222 for delivery to the skin layer.

As a variation, the electrode assemblies 210, 212 may both be capable of retaining the active agent to dispense, but the electrode assemblies 210, 212 may have differing constructions. For example, the contact layer and amount of active agent 202 each electrode assembly 210, 212 can retain may be different.

In contrast to an embodiment of FIG. 1, the alternating source 208 is electrically connected to cause dispersion of active agent 202 from both electrode assemblies 210, 212 in alternating fashion. In one embodiment, the alternating power source 208 alternates the power signal to each electrode so that the delivery durations form each electrode assembly are the same. Such a configuration enables delivery durations to alternate between electrode assemblies. Among other benefits, alternating the delivery durations between electrode assemblies enables continuous transdermal delivery of active agents using alternating points in the user's skin, to avoid, for example, skin irritation or saturation.

Similar to prior embodiments of FIG. 1, an embodiment such as described with FIG. 2 may be constructed as a device or kit that can be assembled and deployed for use by the user. Accordingly, one or more housing segments may be incorporated to integrate the electrode assemblies 210, 212 and/or power source 208.

Figure 3:
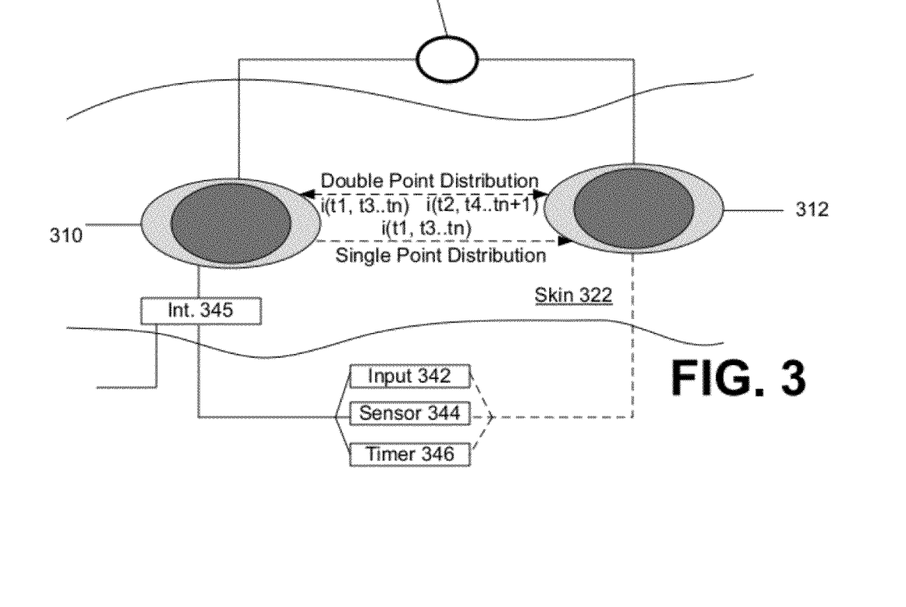
FIG. 3 is a top view of the electrode assemblies deployed on a skin layer of the user.

FIG. 3 is a top view of the electrode assemblies deployed on a skin layer of the user. The electrode assemblies 310, 312 may be implemented to disperse an active agent from one electrode assembly (single point disbursement, such as described with FIG. 1) or from both electrode assemblies 310, 312 (double point disbursement, such as described with FIG. 2). In a single point disbursement configuration, the alternating power source 308 repulses the active agent into the skin 322 (into the paper, as depicted by Z axis) in alternating durations when the supplied current has the same polarity as the charge of the active agent. As mentioned elsewhere, the alternating durations may last milliseconds, seconds, or minutes. The alternating durations may also be asymmetrical or unequal in duration. In a single point disbursement, for example, current is extended from the alternating power source 308 through the contact thickness (see element 118 of FIG. 1) of the first electrode assembly 310, into the skin layer 322, and to the second electrode 312 (serving as the return) to form a circuit with the alternating power source 308. The active agent is thus dispensed from one electrode assembly 310 into the skin layer in alternating durations (durations marked by $t_1$, $t_3$, $t_n$) set by the frequency of the current from the power source 108. Significantly, the active agent does not dispense passively in the alternating instances when the polarity of the current is opposite to the charge (i.e. attractive polarity) of the active agent (durations marked by $t_2$, $t_4$, $t_{n+1}$). In that instance, the opposite polarity of the current/voltage serves as a retention mechanism of the active agent within the electrode assembly 310.

In a double point disbursement configuration (such as described with an embodiment of FIG. 2), the alternating power source 308 alternates which electrode assembly is directing the active agent into the skin layer 322. In one implementation, for example, both electrode assemblies may carry the active agent, and the active agent is positively charged. At a first duration when the current has a positive polarity, (i) a positively charged active agent in the first electrode assembly 310 is directed into the skin layer, (ii) a positively charged active agent in the second electrode assembly 312 is retained, or precluded from being diffused into the skin layer. In the next duration, when the current has the negative polarity, (i) a negatively charged active agent in the first electrode assembly 310 is retained or precluded from being diffused into the skin layer; and (ii) a positively charged active agent in the second electrode assembly 312 is directed into the skin layer. The timing sequence of the first electrode assembly 310 thus may be described as (i) dispense at durations marked by ($t_1$, $t_3$, $t_n$), and (ii) retain at durations marked by ($t_2$, $t_4$, $t_{n+1}$). Likewise, timing sequence of the second electrode assembly 312 may be described as (i) dispense at durations marked ($t_2$, $t_4$, $t_{n+1}$) and (ii) retain at durations marked by ($t_1$, $t_3$, $t_n$).

With regard to either the single or double point disbursement configuration, the frequency of the electrode assemblies operation may be measured in milliseconds, seconds or minutes. For example, in a single disbursement embodiment, a drug-on mode of operation may last several minutes, followed by a drug-off mode. The time periods for the drug-on and drug-off states may be the same or different. For example, the drug-on states may last several minutes, but the drug-off state may be much shorter.

According to an embodiment, the electrode assemblies 310, 312 can be used in connection with the following mechanisms to initiate and/or stop use of the electrode assemblies: (i) input from a user input mechanism 342, (ii) input from a sensor 344 or sensor system for detecting a human/physiological condition, and/or (iii) a timer 346. A user input mechanism may correspond to a switch, button or similar mechanism that the user can trigger. The user input mechanism 342 may be used to initiate use of the electrode assemblies 310, 312 once the user places the electrode assemblies on his skin. The user input mechanism 342 may also be used to stop the electrode assemblies at the user's election. For example, the user may deploy the electrode assemblies on his skin layer, then press a button or cause the power source to power the electrodes at a desired time.

The sensor 344 (or sensor system) may correspond to a physiological sensor that triggers the electrode assemblies to operate when the sensor 344 detects a physiological condition. For example, the sensor 344 may correspond to a glucose monitor for diabetics; the glucose conditions trigger sensor 344 to actuate the electrode assemblies.

As an alternative or variation, a system such as described with FIG. 3 may be provided with an interface 345 to enable the power source 308 to be triggered or operated by the output of sensor 344 or other sensor. In this way, a system such as described by various embodiments may be deployed in an environment where the user has one or more pre-existing body sensors to detect various conditions. The interface 345 may include logic or circuitry to enable interpretation of the sensor output from the user's sensor system.

The timer 346 corresponds to a mechanism, implemented by, for example, logic or circuitry, that (i) switches the power source 308 from a state of delivery (i.e. signal current output to the electrode assemblies) to a state of non-delivery through current/voltage output; and/or (ii) switches the power source 308 from a state of non-delivery (i.e. signal reverse current or no current) to a state of delivery. In a typical implementation, the timer 346 may switch the power source 308 into a state in which the current output matches the charge of the active agent for a set duration, then switch the power source to either turn off or output a reverse current.

As an alternative or variation to embodiments described, the sensor 344 or sensor system is configured to trigger electrode assemblies 310, 312 to cease operation when a physiological condition is no longer present. As still another variation, rather than switch off, an embodiment may switch the mode of operation of the electrode assemblies from a drug deliver to a drug-off state. The drug-off state differs from an off state, in that a reverse current may be used to (i) maintain the electrodes in the deployed state, but (ii) retains the active agent with the electrode as a result of the polarity of the current. For example, with reference to an embodiment of FIG. 1, when the sensor 344 detects presence of the physiological condition, the electrode assembly 310 switches on to deliver a type of active agent to address the condition. After the physiological condition is being detected as being treated (either by sensor or timer), the electrode assembly 310 switches into a reverse current state, so that no drug is delivered into the skin layer. Subsequent re-occurrence of the condition may trigger the first electrode assembly 310 into the drug delivery mode again upon the sensor 344 detecting re-occurrence of the physiological condition.

Various embodiments described above provide for alternating current/voltage to drive a charged active agent from an electrode assembly into the skin layer of the user. Embodiments further recognize that a waveform of the alternating current/voltage that is output from the alternating power source may be of consequence as to the operation and application for the transdermal iontophoretic delivery system described by various embodiments. Numerous current output waveforms and applications for using such waveforms are described with FIG. 5A through FIG. 5F.

Applications and Waveforms

Figure 4:
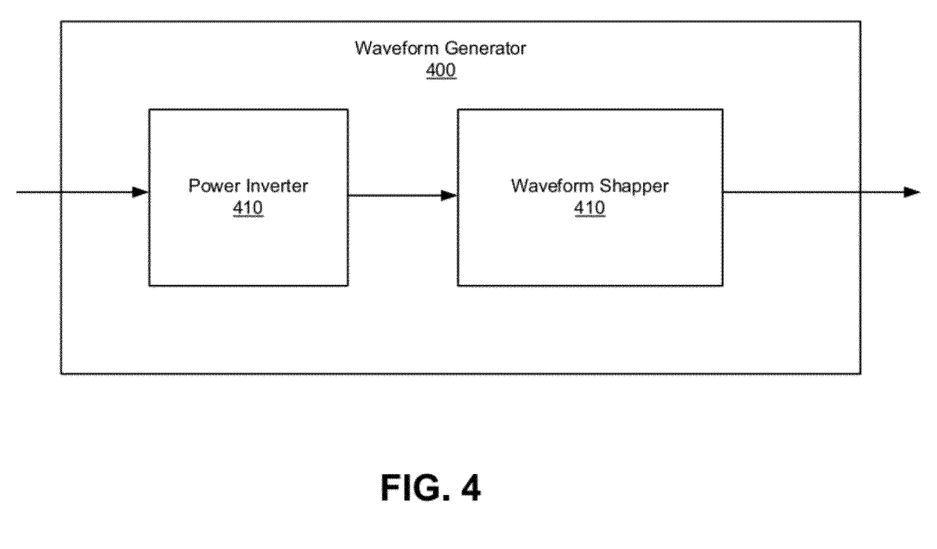
FIG. 4 illustrates an alternating power source for use with embodiments such as described with FIG. 1 though FIG. 3.

FIG. 4 illustrates an alternating power source for use with embodiments such as described with FIG. 1 though FIG. 3. The waveform generator 400 has an input to receive a DC current from a battery (or other power source, such as photovoltaic solar cell) and converts the input into a shaped waveform. Examples of the shaped waveform may be a sinusoidal waveform, a square waveform, a trapezoidal waveform, or other similar waveforms. Some waveforms, such as square waves, in particular, may short or long frequency. Short frequency waveforms may repeat several times per second (e.g. 1/60 seconds), while long frequency waveforms may repeat once over several minutes (e.g. 20 minute). In generating the waveforms, some embodiments use a voltage that is in range of 1 to 100 volts.

The waveform generator 400 includes power inverter 410 and waveform shaper 420. Power inverter 410 has an input to receive the DC current and an output to transmit an AC current to the waveform shaper. The waveform shaper 420 includes circuitry to shape the AC current to the desired waveform. For example, the waveform shaper 420 may include capacitive or inductive elements in order to obtain the desired shape of the waveform. The shaped waveform is outputted by the waveform generator 400.

FIG. 5A through FIG. 5F illustrates various waveforms or current output variations (over time) that can be used to promote a characteristic of the electrode assemblies operation on a user's skin. Embodiments such as described may be implemented in either a single (see FIG. 1) or double (see FIG. 2) disbursement configuration. In describing an embodiment of FIG. 5A-5F, reference may be made to elements or numerals of FIG. 3 for purpose of illustration. Numerous embodiments described herein provide for waveforms that vary between a given polarity and zero, wherein at polarity, the current causes the active agent to repel in the skin layer. In other embodiments, the waveforms have alternative between positive and negative polarity. In some embodiments, the alternating currents can be delivered to each electrode assembly that is in use (whether or not the electrode assembly has the active agent). By orienting the waveform to alternate in charged-balance fashion, electrical toxicity or damage to the skin can be reduced or minimized. In other embodiments, an alternating current is used that is oriented towards being balanced in charge, but some asymmetry may exist.

The waveforms described below are variable between a minimum and maximum value. Some embodiments, such as described with FIG. 5B, may be alternating in charge value (i.e. include reverse polarity). In such embodiments, the current delivery may be balanced in charge.

Figure 5A:
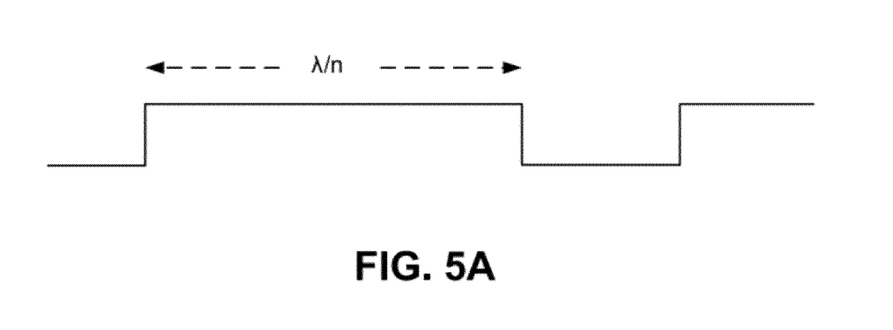
FIG. 5A through FIG. 5F illustrate various waveforms or current output variations that can be used to promote a characteristic of the electrode assemblies operation on a user's skin.

FIG. 5A illustrates a waveform 510 that includes an extended or long drug delivery phase, according to an embodiment. In some embodiments, the skin layer may be assumed to handle only a maximum amount of current in a given duration (max current delivery) (e.g. 80 milliamps per minute). For a given amperage, the duration of the output of the alternating power source may be set to not exceed the max current delivery. The delivery duration may be set to some portion or fraction (e.g. 50% for n=2) of the overall period of the current output $I_1$. For example, in some implementations, the max current delivery ($I_1$) is assumed to be 80 milliamps for one minute. In such an implementation, the delivery duration is set for 20 seconds on 4 milliamp output. Rather than switch to negative polarity, the output of the power source 308 may alternate to no amperage output (rather than switch polarity). While the waveform depicted in FIG. 5A is rectangular, the waveform may have an alternative shape (e.g. sinusoidal, trapezoidal), with the current delivery corresponding to the area under the curve. In the example shown by FIG. 5A, the alternating power source 308 initiates a delivery duration on one electrode, with delivery durations being set by a current that has a polarity that matches that of the charge of the active agent. The current may alternate to zero output, in which the drug delivery is substantially ceased. Thus, the no-delivery duration may coincide with no current output, rather than reverse current.

Figure 5B:
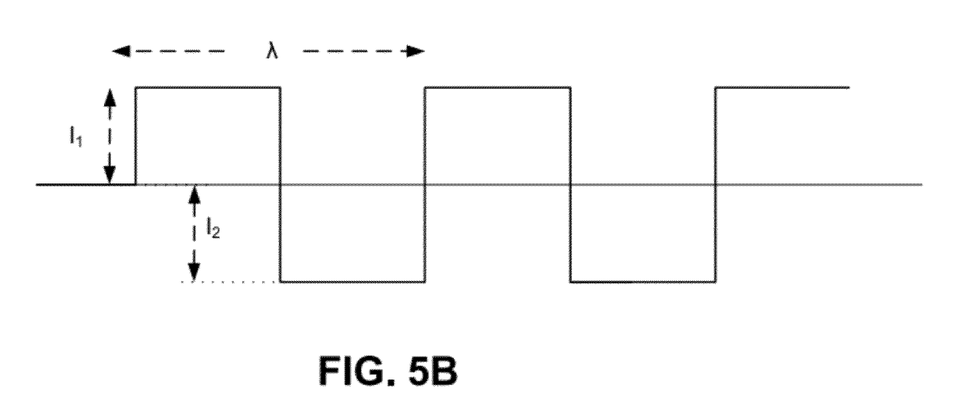

FIG. 5B illustrates another embodiment in which the alternating power signal outputs a symmetrical square wave. FIG. 5B (and other waveforms illustrated herein) illustrate use of charged balance alternating currents. For example, symmetrical waveforms in polarity may be considered as charged balance. Depending on the application, the cycle may be long (e.g. 20 minutes) or short (1/60 of a second). The delivery duration may correspond to half of the period of the waveform. In the implementation shown, a reverse current is used to in the non-delivery duration, to actively prevent agent delivery to the skin layer.

Figure 5C:
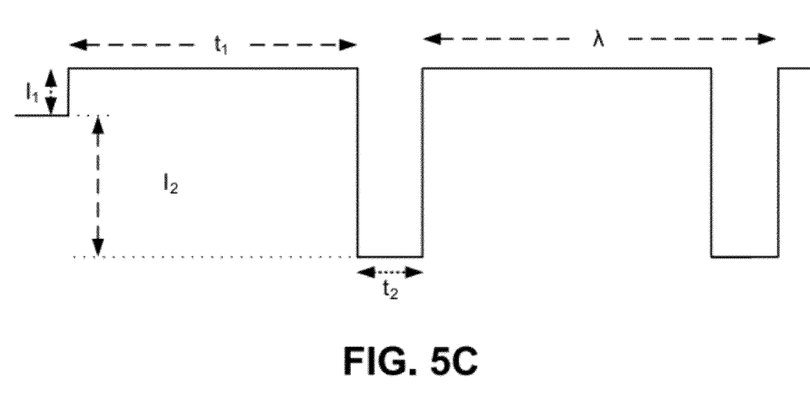

FIG. 5C illustrates another embodiment in which the alternating power signal outputs an asymmetrical square wave, in that the delivery duration is different than the non-delivery duration. More specifically, the asymmetrical square wave may include longer delivery durations ($t_1$), followed by short(er) rest durations ($t_2$). The rest durations may correspond to periods of no current, or as shown, reverse current ($I_2$). In one application, the rest duration enable the skin layer to recuperate from the drug delivery in the prior duration (e.g., to dissipate any heat, concentration of ions, or other by products resulting from the delivery of current). As an alternative or variation, the rest period may follow a period where no current is applied to the skin layer, so as to enable the skin layer to recuperate from application of current.

Figure 5D:
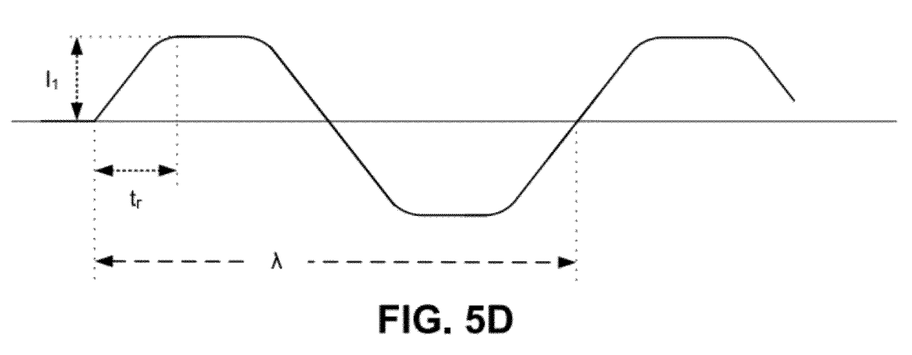

FIG. 5D illustrates another embodiment in which the alternating power signal is trapezoidal, so as to include a ramp-up and/or ramp-down. As depicted, $I_1$ is the maximum current output generated from the power source 308. The ramp-up period extends for a duration $t_r$, selected for reasons that include enabling the user to physically accustom to the application of current and/or active agent. The period may be long, to enable the ramp-up duration to be effective. In an embodiment, a ramp-down period may optionally be implemented.

Figure 5E:
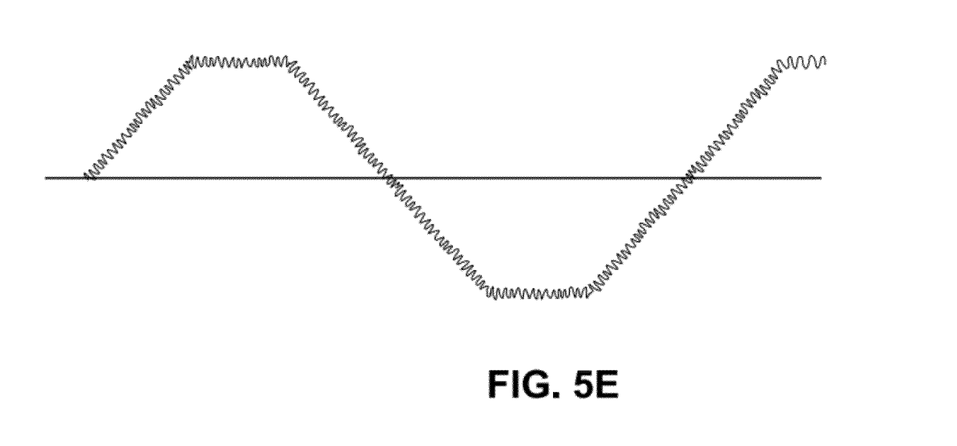
Figure 5F:
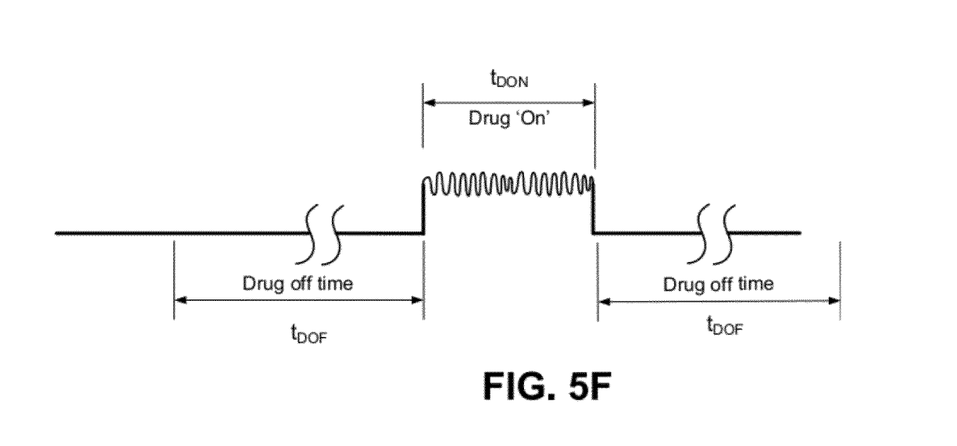

FIG. 5E and FIG. 5F illustrate alternative waveform variations in which high-frequency oscillations are superimposed on a base waveform. The base waveform may have a period that lasts seconds or minutes, corresponding to output current to the electrode assemblies ranging from a maximum (e.g. 4 MA) to no current and/or reverse current. The high-frequency oscillations reflect small variations in the current value at instances in the period. The period of the high-frequency oscillations may be one or more magnitudes shorter than that of the base waveform. As an example, the base waveform may have a period ranging seconds to minutes, and the high-frequency oscillations of the waveform may have a period that ranges between milliseconds and seconds. The effect of the high-frequency oscillations is to reduce the effects of the capacitive charge in the skin layer in receiving the active agent. The high frequency oscillations may also be used to facilitate transport of the active agent through the skin including the stratum corneum by causing oscillations in the movement of the active agent as it travels through the skin so as to find pathways of least resistance through skin. In such embodiments, the high frequency oscillations may be adjusted to enhance this effect through use of modeling (e.g., pharmacokinetic modeling) and/or the patients age, skin type and skin location The base waveform may be selected for considerations such as described in prior embodiments. For example, in FIG. 5E, the waveform includes a ramp-up time period. In FIG. 5F, the waveform has a delivery duration that is switched to a non-delivery duration. An embodiment of FIG. 5F illustrates that the high-frequency oscillations may be generated to be present only during the delivery duration.

Applications

Numerous applications exist for embodiments described herein. Table 1 lists, for example, various medical conditions that may be treated with various drugs and other active agents, using a system of electrode assemblies such as described above. The table further identifies whether the treatment can be patient activated, sensor activated, timed, or continuous. If patient activated, a user input mechanism 342 (FIG. 3) may be operated by the user when the electrode assemblies are in the deployed state to initiate operation of the electrode assemblies (and delivery of the active agent). Examples of user activated applications include delivery of various pain management drugs such as lidocaine or fentanyl. Sensor activated uses may incorporate use of one or more sensors 344 that interface with the user's body to determine whether a condition of the user requires treatment with the identified active agent. An example of a sensor activated application can include treatment of diabetes where the sensor is a blood glucose sensor or (other sensor means for detecting hyperglycemia) and administers a dose of insulin. A treatment is timed if it incorporates the timer 346 to determine when to start/stop the delivery durations.

TABLE 1

| Active Agent | Condition | Patient Activated | Sensor Activated | Timed | Continuous |
|---|---|---|---|---|---|
| Insulin | Diabetes | X | X | X | |
| GLP-1/Integrin | Diabetes | X | X | X | |
| $Fe^{2+}$ | Anemia | | | | X |
| Sodium (Na), Potassium (K) | Electrolyte renewal | | | | X |
| Furosemide | Epilepsy | | X | X | |
| Bumetanide | Migraine | X | X | X | |
| Aspirin | Inflammation | X | X | X | |
| Ketoprophin | Arthritis | X | | | |
| Lidocaine | Pain | X | | | |
| Fentanyl | Pain | X | | | |
| Alprazolin | Anxiety/Pain | X | X | | |
| Antibiotics | Wound Healing | | | | X |

In specific embodiments, the active agent can comprise a sufficient amount of elemental iron for the treatment of iron deficiency anemia. The amount of elemental iron can be sufficient to provide between 1 to 100 mg of elemental iron to the patient for a period of days or even weeks. In various embodiments the elemental iron can comprise ionic iron in the form of ferrous ($Fe^{2+}$) or ferric ($Fe^{3+}$) iron. The ionic iron can comprise an iron salt, a ferrous salt, a ferric salt, ferric pyrophosphate ferrous chloride or a combination thereof.

Although illustrative embodiments of the invention have been described in detail herein with reference to the accompanying drawings, it is to be understood that the invention is not limited to those precise embodiments. As such, many modifications and variations will be apparent to practitioners skilled in this art. Accordingly, it is intended that the scope of the invention be defined by the following claims and their equivalents. Furthermore, it is contemplated that a particular feature described either individually or as part of an embodiment can be combined with other individually described features, or parts of other embodiments, even if the other features and embodiments make no mentioned of the particular feature. This, the absence of describing combinations should not preclude the inventor from claiming rights to such combinations.

What is claimed is:

1. A system for transdermal delivery of active agents for therapeutic and medicinal purposes, the system comprising:
    a power source that provides a charged balanced alternating output current that varies between a first current value and a second current value;
    a pair of electrode assemblies, each electrode assembly being configured to be held in contact with a skin layer of a user, and wherein each electrode assembly includes an electrode that is coupled to the power source to receive the output current;
    wherein at least one of the electrode assemblies in the pair includes a medium that carries an active agent having a charge, the medium being provided on the at least one electrode assembly to enable the output current to repel the active agent into the skin layer for a duration in which the output current has a polarity that is the same as a polarity of the active agent; and
    wherein the power source is configured to provide the output current in a waveform that is asymmetrical, so that a duration in which the output current has the polarity that is the same as the polarity of the active agent is longer than a duration when a minimum value of the output current is zero or negative; and
    a re-sealable intake conduit formed upon a surface of the electrode assembly that includes the medium, the re-sealable intake conduit being configured to permit refilling of the medium.

2. The system of claim 1, wherein the output current alternates between instances in which the active agent is repelled and then retained as a result of a polarity of the active agent.

3. The system of claim 1, further comprising a physiological sensor configured to detect a physiological condition of the user.

4. The system of claim 1, wherein the power source is configured to provide the output current in a waveform that includes a ramp-up duration in which a value of the output current is increased to a maximum value.

5. The system of claim 1, wherein the electrode assemblies are constructed to be reusable.

6. The system of claim 1, wherein the re-sealable intake conduit includes a self-sealing port that enables the active agent to be readily dispersed in the medium.

7. The system of claim 6, wherein the self-sealing port is formed from an elastomeric material.

8. The system of claim 1, wherein the electrode assembly including the medium further includes a tissue contacting porous layer configured to absorb the active agent from the medium and introduce the active agent into the skin layer.

9. The system of claim 8, wherein the tissue contacting porous layer has a selected porosity based on a molecular characteristic of the active agent.

10. The system of claim 1, further comprising:
    a user-activation means coupled to the power source to enable the user to trigger the power source and actuate the electrode assemblies.

11. The system of claim 1, wherein the active agent is one of a drug, and antibiotic, an anti-diarrheal agent, an insulin compound, or a vaccine.

12. The system of claim 1, wherein the active agent is one of an iron salt, a ferrous salt, a ferric salt, a ferric pyrophosphate, or a ferrous chloride solution.

13. The system of claim 3, wherein the physiological sensor is configured to trigger the power source to actuate the pair of electrode assemblies.

14. The system of claim 13, wherein the physiological sensor is configured to trigger the power source to actuate the pair of electrode assemblies when the physiological condition of the user crosses a predetermined threshold.

15. The system of claim 14, wherein the physiological sensor is a glucose monitor, and wherein the physiological condition corresponds to a blood-sugar level of the user.

16. The system of claim 15, wherein the active agent is one of ionized insulin or an ionized glucagon-like peptide-1 agonist.

17. The system of claim 14, wherein the physiological sensor is further configured to automatically deactivate the power source once the physiological condition has been normalized.

* * * * *